US008691273B2

(12) United States Patent
Rudin et al.

(10) Patent No.: US 8,691,273 B2
(45) Date of Patent: Apr. 8, 2014

(54) METHOD FOR PRODUCING HYDROXYAPATITE PARTICLES

(75) Inventors: Vsevolod Nikolaevich Rudin, Moscow (RU); Igor Vitallevich Melikhov, Moscow (RU); Vladimir Vasillevich Minaev, Moscow (RU); Andrei Yurievich Orlov, Moscow (RU); Viktor Evgenievich Bozhevolnov, Moscow (RU)

(73) Assignee: Lisopharm AG (LI)

( * ) Notice: Subject to any disclaimer, the term of this patent is extended or adjusted under 35 U.S.C. 154(b) by 1304 days.

(21) Appl. No.: 11/996,254

(22) PCT Filed: Jul. 21, 2005

(86) PCT No.: PCT/EP2005/007951
§ 371 (c)(1),
(2), (4) Date: Oct. 22, 2008

(87) PCT Pub. No.: WO2007/009477
PCT Pub. Date: Jan. 25, 2007

(65) Prior Publication Data
US 2009/0155320 A1 Jun. 18, 2009

(51) Int. Cl.
*A61K 9/10* (2006.01)
*A61K 38/18* (2006.01)
*A61K 9/70* (2006.01)

(52) U.S. Cl.
USPC .................. 424/484; 424/492; 106/160.1

(58) Field of Classification Search
USPC ....................................................... 424/423
See application file for complete search history.

(56) References Cited

U.S. PATENT DOCUMENTS 5,766,247 A * 6/1998 Aoki et al. .................... 424/423
2005/0271695 A1 * 12/2005 Kikuchi et al. ............... 424/423

FOREIGN PATENT DOCUMENTS

| EP | 0 431 672 A | 6/1991 |
| JP | 08 336584 A | 12/1996 |
| WO | 92/00109 A | 1/1992 |
| WO | 98/30318 A | 7/1998 |

OTHER PUBLICATIONS

"European Office Action for European Application No. 05 762 948. 7", Jan. 25, 2011, Publisher: European Patent Office, Published in: EP.
Rhee S-H et al, "Biomimetic configurational arrays of hydroxyapatite nanocrystals on bio-organics", Biomaterials, Elsevier Science Publishers BV., Barking, GB, vol. 22, No. 21, Nov. 2001, pp. 2843-2847, XP004298285, ISSN: 0142-9612.
Chang M C et al, "Preparation of hydroxyapatite-gelatin nanocompoiste", Biomaterials, Elsevier Science Publishers BV., Barking, GB, vol. 24, No. 17, Aug. 2003, pp. 2853-2862, XP004424098, ISSN: 0142-9612.
Gosain Arun K et al, "A 1-year study of asteoinduction in hydroxyapatite-derived biomaterials in an adult sheep model: PArt I", Database Medline 'Online!, US National Library of Medicine(NLM), Bethesda, MD, US, XP002350034, Database accession No. NLM11818845, Plastic and Reconstructive Surgery, vol. 109, No. 2, Feb. 2002, pp. 619-630, ISSN: 0032-1052.
Zhai Y et al, "Formation of nano-hydroxyapatite on recombinant human-like collagen fibrils", Current Applied Physics, North-Holland, vol. 5, No. 5 Jul. 2005, pp. 429-432, XP004914142, ISSN 1567-1739.

* cited by examiner

*Primary Examiner* — Walter Webb
(74) *Attorney, Agent, or Firm* — Kaplan Breyer Schwarz & Ottesen, LLP

(57) ABSTRACT

This invention relates generally to a preparation of bone repair compositions, and more special refers to a novel technology in preparing a matrix building polymer i.e. collagen with inclusions of hydroxyapatite particles as biomaterial for medical applications. In this composition that consists of hydroxyapatite particles embedded in a matrix at least 50% nm. Said composition is suitable as bone implant material, dental cement and for applications in wound healing.

14 Claims, 10 Drawing Sheets

METHOD FOR PRODUCING HYDROXYAPATITE PARTICLES

FIELD OF THE INVENTION

The invention relates to a method for producing hydroxyapatite (HAP) with the chemical formula $(Ca_{10}(PO_4)_6(OH)_2$—"HAP") particles, in particular subnanodisperse hydroxyapatite particles and a biocomposite material.

BACKGROUND OF THE INVENTION

This invention relates generally to a preparation of bone repair compositions, and more special refers to a novel technology in preparing collagen with inclusions of hydroxyapatite particles as bone repair compositions. This biocomposite material is designed for application as implant or growth stimulator of bone tissue in bone surgery, surgical stomatology, orthopedy, traumatology, reconstruction-restoration surgery and other fields of medicine.

One of the most important challenge, when producing a preparation which shall be used in reconstructive surgery, is to produce a substance with a chemical composition and parameters that are identical or nearly similar to the basic substance of the living organism. It has long been understood, that bone is composed of living cells, an organic matrix, and a mineral phase. About 95% of the organic matrix consists of the fibrous, matrix building protein collagen I, and the inorganic phase is mainly composed of calcium and phosphate in the form of crystalline hydroxyapatite. The mechanical properties of bone are governed by this perfect adapted composite structure. Whereas the mineral phase creates a high stiffness and compressive strength, the collagen matrix causes high fracture toughness.

The remodeling and repair processes in bone are strictly controlled by cellular activity of osteoblasts and osteoklasts. These cells are able to absorb and synthesize bone material to a limited extend. In order to produce bone-like implant material in medicine, especially in bone surgery, the bioceramic hydroxyapatite has found worldwide practical for the application at the human or mammalian body. Hydroxyapatite is one of the few bio-compatible mineral substances attracting a constant interest to its synthesis and properties. Different methods where developed for synthesizing HAP with different shape, porosity and size of crystals.

A known method of HAP production is described in the document PCT/IB 00/01232 where HAP particles with a length $l=0.06$ µm, width $d=0.015$ µm and thickness h corresponding to a crystal cell parameter equal to $h=0.000688$ µm or $0.000814$ µm depending in the direction of the symmetry of the crystal cell are produced. The process is carried out in aqueous solution in three steps with a separation and concentration of suspension to produce paste or dry powder.

However, one disadvantage of this method is that the plate particles are produced with relatively large length and wide dimensions, i.e. having a relatively large size.

Therefore a wide range of materials has since been utilized, and elaborate designs have been disclosed for replacements of entire portions of bones, e.g., for hip joints (U.S. Pat. No. 3,820,167) and teeth (U.S. Pat. No. 4,186,486). Shaped and treated bone (U.S. Pat. No. 3,318,774), and various bone preparations such as bone dust compacted and flexible mats (U.S. Pat. No. 2,261,145) are used in as a bone-substitute, too. The aforementioned gold standard treatment, autogenous bone graft, with its good biological properties, adequate structural support and osteoinductiveness, has limitations and disadvantages because of the donor site morbidity, limited donor bone supply, anatomical and structural problems, high resorption levels during healing and high economical costs and hospitalization time. Other materials employed have included such as titanium (EPO Pub. No. 00712242), hydroxyapatite or ceramic such as aluminium oxide (U.S. Pat. No. 3,919,723). These materials however have drawbacks either, such as failure for complete bone ingrowth, extended inflammatory reaction and mechanical failure.

Among the potential substitutes another approach is mentioned in the paper "Biomimetric Mineralization of Collagen by Combined Fibril Assembly and Calcium Phosphate Formation" (Chem. Mater. 1999, 11, 2694-2701). There the synthesis of mineralized collagen is carried out by mixing of two solutions. First an aqueous solution containing $CaCl_2$ and second an aqueous solution, actually being aqueous buffer solution containing potassium phosphate, NaCl and a HAP crystallization regulator. As a result the collagen fibrils mineralized with hydroxyapatite are produced with the HAP particle size to about 100 nm. The synthesis is carried out from 2 to 8 hours depending on the conditions. However, one of the main disadvantages of this known method is the production of relatively large size (100 nm) of hydroxyapatite particles and also the long synthesis time. Moreover, according to this method mineralized collagen is produced in narrow range of ratio HAP/collagen.

An object of the present invention is to provide a method to produce small hydroxyapatite particles effective and fast. Further object is to produce small hydroxyapatite particles in a matrix and to manufacture a novel implant material for bone surgery with a high biocompatibility.

The object is achieved by a method incorporating the features of Claim 1 wherein hydroxyapatite particles, in particular subnanodisperse hydroxyapatite particles are produced in a matrix in a method which comprises the steps of suspending a matrix building polymer in a solution forming a suspension, subjecting said suspension to a mechanical action and adding a solution of phosphoric acid and calcium hydroxide for synthesizing hydroxyapatite particles in the presence of the matrix building polymer. It turned out that a method comprising the steps of mixing and holding said suspension in a reactor thereby adjusting a defined alkaline pH value is advantageous. The amount of the matrix building polymer and aqueous solution of calcium hydroxide is controlled to achieve a required ratio of hydroxyapatite particles per matrix. As a result this composition comprises hydroxyapatite particles in the matrix, whereby in this porous sponge mass of composite both components were bond state by the adsorption forces on the molecular level or in a result of co-crystallization. The resulting biocomposite material is well suitable for medical treatments. Moreover said product comprises a very high uniformity and is cost effective, easy, fast and reproducible to manufacture.

According to the invention the matrix building polymer is a framework forming polymer in particular a fibrous protein, that encloses the hydroxyapatite particles. For this purpose proteins, polypeptides, fibrous biopolymers and any type of fibric proteins of collagen group are suitable matrix building polymers. Collagen may be replaced by gelatin or a comparable fibrous biomaterial to obtain a biocomposite material with similar properties and to gain a wider variety for the medical application of the above mentioned biocomposite material. Moreover the use of polysaccharides or derivates of polysaccharides as matrix building polymers is advantageous. In a preferred embodiment of the present invention the use of members of chitin like substances like chitosane is possible, too.

Furthermore the use of a mixture of the matrix building polymeric substances mentioned above, is possible.

According to the invention the present invention provides a novel manufacturing process for hydroxyapatite particles in a matrix, in particular a matrix of collagen, which produces a product with a high uniformity. According to the production of said biocomposite material it turned out, that it is favorable when the ratio of calcium hydroxide and phosphate in the suspension is 1.67±0.3 at the beginning of the hydroxyapatite particle synthesis. In view of temperature during synthesis of the hydroxyapatite particles a temperature between 1° C. and 45° C., preferred between 10° C. and 35° C. and particularly preferred between 20° C. to 25° C. is best suitable.

In the process it turned out, that it is favorable if the synthesis of the hydroxyapatite particles is carried out comprising the three steps of mixing and holding the suspension comprising the calciumhydroxide, the matrix building polymer and the phosphoric acid in a first mixing reactor (the first stage of mixing) with intensive stirring at $Re \approx 10^4$ thereby adjusting a defined alkaline first pH value of 8 to 9, feeding the suspension into a second reactor (the stage of complete substitution) for production of hydroxyapatite particles and causing a phase transformation of the suspension, and feeding the suspension into a third reactor (the second mixing stage) for mixing the suspension at a defined second pH value to then feed the mixture into a first reactor. Each of these steps is cyclically carried out in defined continuous periodical conditions within at least three stages thereby producing uniquely defined stoechiometric crystalline hydroxyapatite particles of chemically pure hydroxyapatite in a matrix.

As a result, by directing the production of hydroxyapatite particles and the matrix building polymer in the aforementioned predetermined crystallization route hydroxyapatite particles in the suspension are produced, such that the concentration of the fraction of the hydroxyapatite particles wherein more than 50%, 70% or preferably 90% of the particles are smaller than 3.5 nm. Preferably the fraction with a size from 0.35 nm to 5 nm is more than 50%, 70% or preferably 90% or the fraction from 0.35 nm to 2.5 nm is more than 50%, 70% or preferably 90%, or the fraction from 0.35 nm to 1.2 nm is more than 50%. In particular "smaller than" is to be understood as the particles having an overall size or length smaller than the given volumes or being within the given ranges, respectively.

According to the invention in general the synthesis of hydroxyapatite particles in the collagen matrix is carried out under different conditions by:
(a) Mixing a collagen solution in $H_3PO_4$ with $Ca(OH)_2$ accompanied by co-crystallization of collagen and hydroxyapatite particles.
(b) Mixing a solution of collagen in a mixture of $H_3PO_4$ and HCl with a solution of $Ca(OH)_2$ and NaOH to gain hydroxyapatite particles embedded in a matrix consisting of collagen and/or in the fibers.
(c) Mixing a two component solution comprising collagen in $Na_3PO_4$ and water with a solution of $CaCl_2$ to gain a co-crystallization of collagen and hydroxyapatite particles.
(d) Mixing a collagen solution in $H_3PO_4$ with $Ca(OH)_2$ as in method (c) and repeat mixing the product with the aqueous solution of collagen.

As a result a biocomposite comprising collagen and hydroxyapatite particles in different compositions is producable. This suspension, comprising the biocomposite material may be produced either as a paste with any ratio of hydroxyapatite particles/collagen or as a porous or as a powder mass. A matrix building polymer for example collagen of different compositions and concentrations mineralized with hydroxyapatite particles with the chemical formula is designed for application as implant material in bone surgery, orthopedics, traumatology, reconstruction-restoration surgery and other fields in medicine.

The present invention is described as follows in view of two preferred embodiments of methods for synthesis of the hydroxyapatite particles in a matrix of collagen.

The first preferred embodiment of the method according to the invention for producing the aforementioned subnanodisperse hydroxyapatite comprises the steps of intense mixing of an aqueous solution of calciumhydroxide and an aqueous solution of collagen in phosphoric acid in a first reactor, i.e. a mixing reactor. Preferably the formation of the hydroxyapatite particles takes place at a molecular ratio Ca/P=1.67.

In a preferred embodiment the mixing is carried out with the Reynolds number $R \approx 10^4$ by means of a blade mixer for about 15 min with a flow velocity between 10 m/s and 20 m/s. The ratio of hydroxyapatite particles/collagen is determined by the amounts of calcium hydroxide and collagen introduced into the reaction.

According to the invention the holding time after mixing is about 30 min. This holding time is advantageous to convert the primary composition of particles of calcium phosphates to hydroxyapatite particles according to the scheme DCP→OCP→TCP→HA (where DCP—dicalciumphosphate—$CaHPO_4$, OCP—octacalciumphosphate ($Ca_8H_2(PO_4)_6$), TCP—tri calcium phosphate $Ca_3(PO_4)_2$). The final pH value of the composition is 6 to 8.

According to this procedure a suspension of separate or particularly aggregated hydroxyapatite particles in collagen with sizes from 2 to 1000 nm, preferably 10 to 300 nm is produced where its bulk includes subnanoparticles (SNP) of HAP of given size.

Afterwards the separation and concentration by means of filtration or centrifugation or other methods to remove water and byproduct electrolytes, for example, by means of membrane technology at temperatures not exceeding 40° C.

In a result a paste is produced that presents a composition with a concentration of a sum of substances of collagen and hydroxyapatite particles from 5 to 30% by weight. During drying by means of lyophylic or sublimation drying processes a paste with any ratio of collagen/hydroxyapatite-water with concentration of a sum of substances of collagen and hydroxyapatite of more than 30% is produced. This paste may be used in medicine. Complete drying of the paste produces an anhydrous porous powder mass depending on the collagen content. This powder may be used in medicine, as well.

In a second preferred embodiment of the method according to the invention hydroxyapatite is produced in a method similar to process 1 to gain higher yields of subnanosized hydroxylapatite particles. This periodical process is carried out in three steps.

In a preferred embodiment the first reactor, i.e. a first mixing reactor is filled with aqueous solution of aqueous collagen phosphate solution and an aqueous suspension of calcium hydroxide taken in ratio Ca/P=1.67. The content of collagen and calcium hydroxide is regulated for producing the required ratio of HAP/collagen taking into account solubility of collagen in phosphoric acid.

According to the invention the holding time is shorter than 5 s, preferably about 0.2 s to 0.8 s, and the mixture is stirred with a flow velocity between 10 m/s to 20 m/s to achieve a complete homogenization of the medium components.

If the holding time is more than 0.8 s the formation of larger particles (up to 15-20 nm) is possible because aggregation of the primary subnanocrystals would proceed in the conditions of high hydrodynamics. At a holding time less than 0.2 s the formation of the primary subnanoparticle and their complexing with collagen is not complete.

At flow rates less than 10 m/s the required level of hydrodynamic conditions is not ensured and complete homogenization does not occur in the product whose size is not homogenized. A flow velocity of suspension larger than 20 m/s is not expedient because it results in increasing power consumption and in complicated technical construction of the first reactor. Though increasing flow rate during mixing does not affect the final product quality. The mixture is kept at a pH of 8 to 9.

At the second stage of the crystallization process that takes place in a reactor of complete substitution the conditions are created for modification of the chemical composition of the primary subnanoparticle with composition $(CaHPO_4)_n$ through octacalcium phosphate and tri calcium phosphate to "$Ca_7(PO_4)_3OH$-collagen" or "$Ca_{10}(Po_4)OH)_2$ Collagen" at the extent of absorbing the Calciumhydroxide. The holding time of 10 s ensures completeness of the transformation of the primary subnanoparticle into hydroxyapatite. A holding time of more than 20 s is not expedient for the transformation process. A pH value in the range between 8 to 9 is optimal for the aforementioned transformation.

In a further preferred embodiment the produced mixture is led into a third stage that takes place in a second reactor of complete mixing. At this stage the saturation of the aqueous phase with calciumhydroxide takes place and pH attains about 12. In technological process the aqueous solution of calcium hydroxide is prepared during mixing the calcium oxide in water with a solid:liquid ratio (S:L) of 1:10 to 1:1000, to define the final concentration of the hydroxyapatite particles. The obtained aqueous mixture HAP-collagen and calcium hydroxide is led into the first stage to where collagen phosphate solution is fed. Then the mixture again is directed into the second and the third stages, whereby the realization of circulation of the whole reaction volume through three reactors is repeated cyclically until calcium hydroxide disappears, preferable completely and an aqueous suspension of HAP-collagen is formed with conservation of the aforementioned condition of the process each stage. The pH value after using calcium hydroxide in the whole volume of suspension is 6 to 8.

The circulation rate is determined by the quantities of reacting components, the holding time of reacting mass in the three stages and also by the indicated flow rates at these stages and it attains 10 to 15. The whole process is carried out at temperatures between 10° C. and 50° C. The characteristic feature of the crystallization of the composite "HAP-collagen" in the present invention is aggregation of collagen particles including hydroxyapatite particles. Their aggregation is proved to be inevitable due to mutual collisions in the intensive hydrodynamic conditions, multifold circulation of the reacting mass and high concentration of the composite particles HAP-collagen. High concentration is necessary for higher productivity if compared with the first method.

It should be noted that production of various ratios of HAP to collagen depends on the collagen solubility in phosphoric acid that limits its possibility of the wide variation of the composition in the final product. Collagen solubility depends on concentration of phosphoric acid and it is 1 to 20% and it is higher if the acid concentration increases. In a synthesis all phosphate ions should be introduced into hydroxyapatite. Therefore using such approach a product may be obtained containing less than 30% of collagen in HAP-collagen matrix if calculated for an anhydrous product. It is an advantage of the present invention that the synthesis results in the final product without any mixture of byproduct electrolyte.

To increase a ratio of HAP to collagen in the whole range, namely from the composition with 0.1% of collagen and 99.9% of HAP to one with 0.1% of HAP and 99.9% of collagen the compositions of the mentioned solution are varied and a mixture of hydrochloric acid and phosphoric acid is used to dissolve higher amounts of collagen. It relates to the fact that the solubility of collagen in hydrochloric acid is higher than in phosphoric acid in 2 to 5 times depending on the type of collagen. Therefore in the first preferred embodiment of the method of synthesis the following solutions are used:
1. Aqueous solution of $CaCl_2$ and NaOH.
2. Aqueous solution of collagen in HCl and $H_3PO_4$.

By controlling the amount of a dissolved collagen and concentrations of HCl and $H_3PO_4$, and as well concentration of $CaCl_2$ and NaOH (the ratio Ca/P is preferably equal to 1.67, and the final pH value is 6 to 8) it is possible to obtain any predetermined ratio HAP/collagen in a solid phase of the HAP-collagen product. Using for example, washing off or membrane technology it is possible to remove completely NaCl. Further separating and concentrating of the product are carried out to produce a paste with predetermined ratio HAP/collagen in the solid phase of the product, and by using the aforementioned means of drying the dry product is prepared with the same ratio of HAP/collagen. The production process itself is carried out under the same conditions as indicated in description of the first preferred embodiment of the method for producing hydroxyapatite particles in collagen.

For the second preferred embodiment of the method of synthesis the following solutions are used:
1. Solution of NaOH in aqueous suspension of calcium hydroxide.
2. Aqueous solution of collagen in HCl and $H_3PO_4$.

According to the invention this process is carried out under the aforementioned conditions for the second preferred embodiment of the method, adding the acidic solution of collagen to the solution of NaOH with calciumhydroxide. In this case by controlling the mass of collagen, $H_3PO_4$, HCl, calcium oxide and NaOH with molar ratio of about Ca/P=1.67 and complete neutralization of acid and alkalis (the final pH is 6 to 8) any required ratio HAP/collagen may be produced. In this case NaCl is formed in the produced mixture. Sodium chloride is removed from the system by means of the aforementioned methods. Further, concentrating the product suspension is carried out to produce the aqueous paste and/or dry product with any predetermined ratio of hydroxyapatite particles/collagen.

According to the invention a hydroxyapatite composition is obtained, comprising hydroxyapatite particles with dimensions from 0.35 nm to 3 nm, wherein the concentration of the fraction from 0.35 nm to 1.2 nm is more than 50% as shown in FIG. 3.

The aforementioned synthetic bone graft material accurately mimics the complex, multi-layered porous structure of a mammalian bone. The material and its particle size have been characterized to maximize the movement and attachment of bone cells within the implant. Recent clinical trials showed that nanocrystalline hydroxyapatite particles in a matrix of collagen results in rapid new bone growth, that is organized, well vascularized and of an extremely high stability.

In a preferred embodiment the bone-like implant material is produced in a different hydroxyapatite to collagen ratio to obtain a material suitable for a wide variety of medical applications.

In an advantageous embodiment said biocomposite material is ideal as bone implant material, dental filling material or dental cement. For this purposes the fraction of hydroxyapatite particles in the matrix of collagen should have a value between 30% and 90% by weight and particularly preferred between 40% and 70% by weight. For the application in the fields of wound healing or tissue engineering hydroxyapatite particle concentrations between 5% and 40% by weight, particularly between 5% and 20% by weight are suitable. In a preferred embodiment of the present invention said biocomposite material is part of a granulated powder, foil, mat, wound dressing, paste or wound healing formulation that is applied on a wound. Thus the migration and proliferation of cells involved in wound healing comprising vascular cells and fibroblasts is promoted and the osteoingrowth and differentation of osteoblasts is stimulated by subnanosized hydroxyapatite. Additional to the aforementioned applications said biocomposite material is suitable as a component of a mineralizing tooth paste or part of dry tablets for oral application for treatment of osteoporosis.

In an advantageous embodiment the implant material is producable in different shapes, thickness and with a variable content of water. The material is producable in form of a plaster of Paris that is biocompatible, bioactive and resorbable after 30-60 days. Moreover the biocomposite material formed as a putty, gel or injectable paste is a suitable filling material in the field of bone repair. In a preferred embodiment the bone-like tissue implant is produced in form of a coating that shows an enormous mechanical strength. It is possible to press or form the coatings to gain an implant material with a defined shape or caliper.

In an advantageous embodiment the bone-like tissue implant is an anhydrous powder which is optionally moulded in different sizes and shapes for various purpose. Preferably it is shaped in a mould which is preferably sealed. The plastic shape of the mould can be designed with computer aided medical image analysis technique which allows to replicate the missing bone structure. According to the invention it is possible to gain a biocompatible moulded pulp product with a variable size, morphology, porosity and geometry.

In a preferred embodiment of the present invention the bone-like implant can be used as a drug-delivery system.

This can be achieved generally by immersing the bone-like implant material in a solution of the desired cell growth factors or drug. Advantageously this results in an effective drug delivery mechanism to deliver high molecular weight proteins or drugs into the bone.

In accordance with the present invention this can be achieved. Thus high molecular weight proteins or drugs incorporated in the bone-like material e.g. in the pores of the subnanosized hydroxyapatit can be released from the bone graft to stimulate osteoingrowth, neovascularisation or to inhibit infections.

Thus growth factors include transforming growth factor (TGF-β), insulinelike growth factors (IGF)I and (IGF) II, plateled derived growth factors (PDGF), fibroblast growth factor (FGF), bone morphogenetic proteins (BMPs), RGD-Peptides, osteogenic protein (OP-1) and others; antibiotics, and other materials including vitamins, trace elements and minerals such as zinc can be incorporated into the bone-like implant material.

BRIEF DESCRIPTION OF THE DRAWINGS

The invention together with its objects may be best understood by reference to the following description taken in conjunction with the accompanying drawings. Features of different examples and embodiments can be combined with each others.

Figure 1:
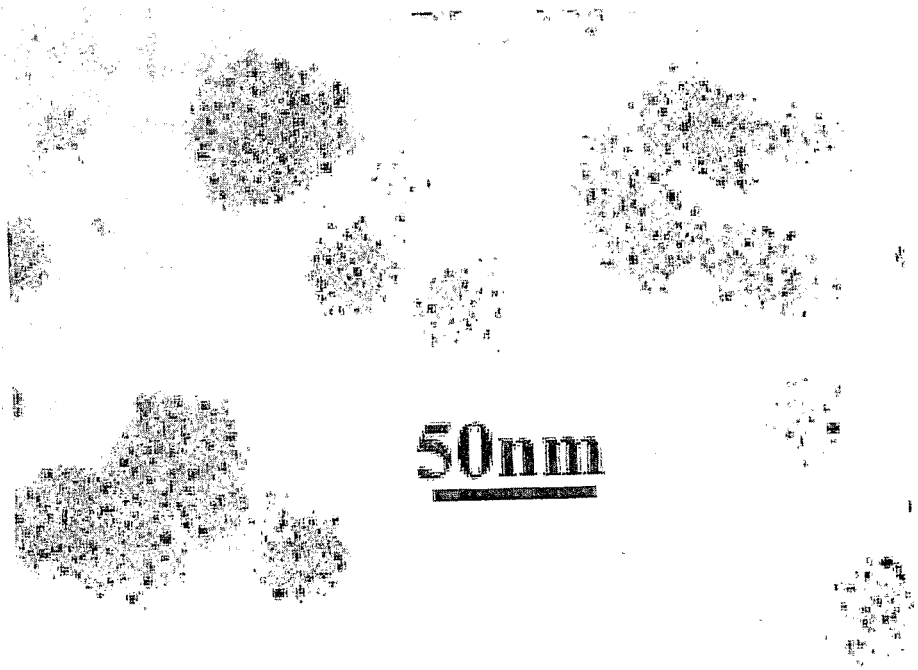
FIG. 1 shows separate or aggregated microparticles of collagen with sizes from 10 to 300 nm where its bulk includes particles of hydroxyapatite.
Figure 2:
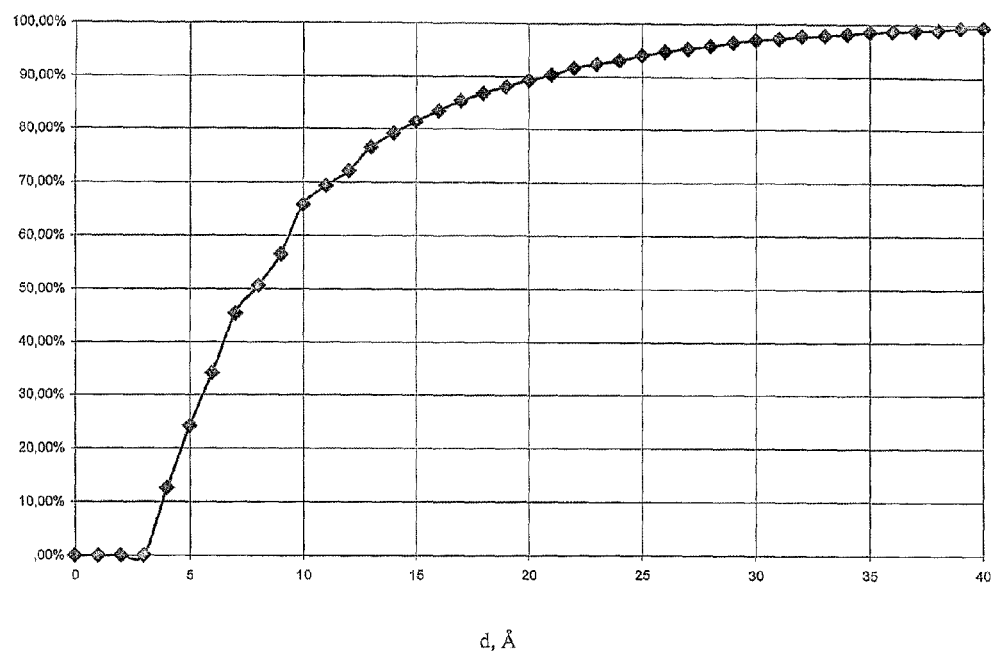
FIG. 2 shows an integral function of the particle size distribution of sizes (in Angstroem) of particles of hydroxyapatite. According to this integral function the composition includes hydroxyapatite particles with dimensions from 0.35 nm to 3 nm, whereby the concentration of the fraction from 0.35 to 1.2 nm is more than 50%.
Figure 3:
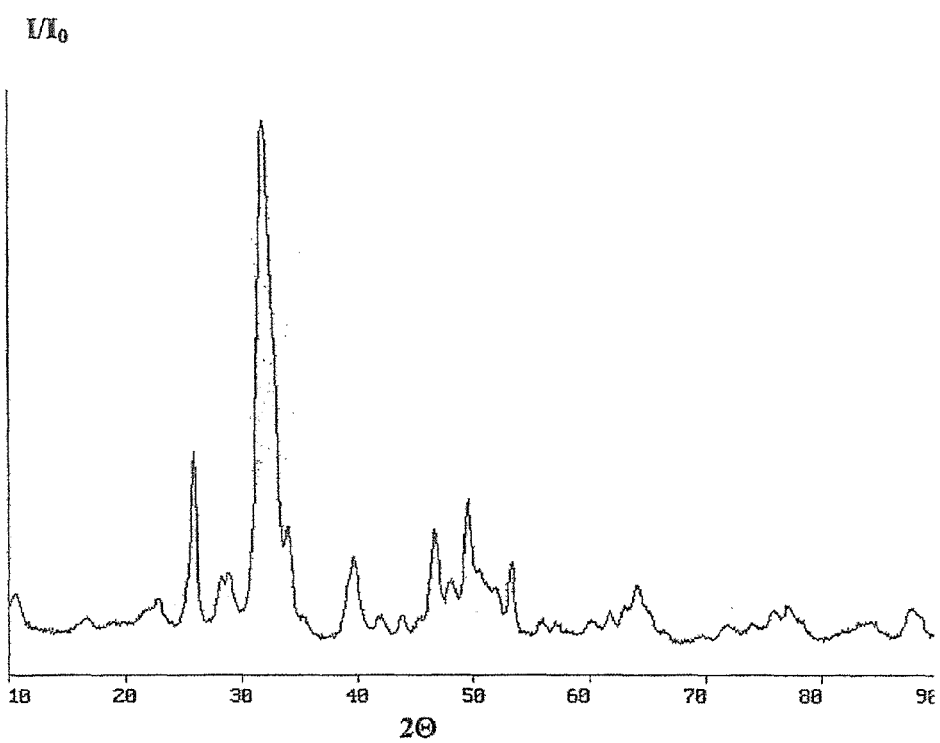
FIG. 3 shows an X-Ray diffraction image of mineralized collagen. The peak positions corresponds to hydroxyapatite particles.
Figure 4:
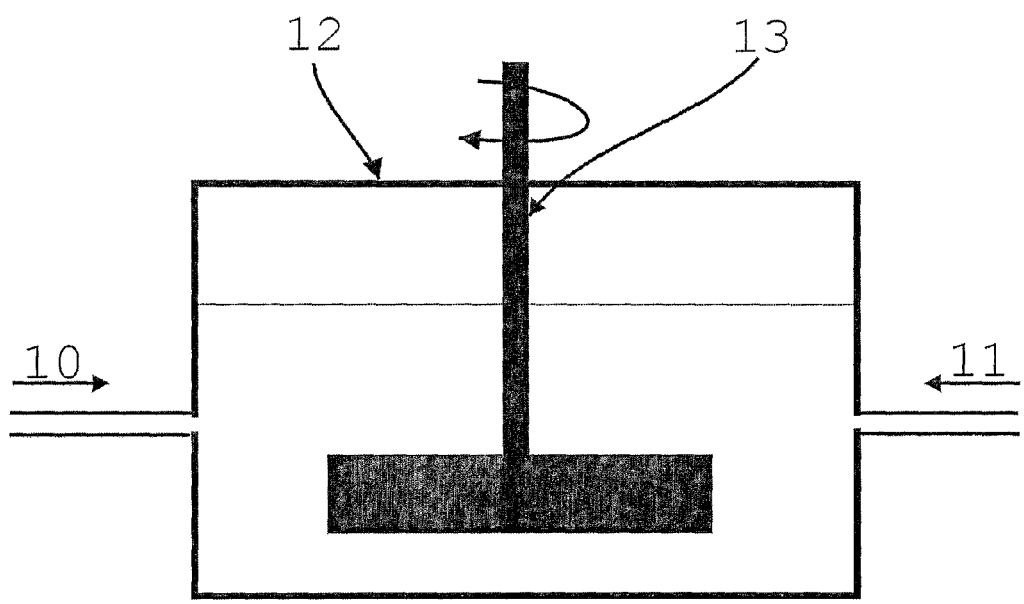
FIG. 4 shows a block-scheme of the first preferred embodiment of the method according to the invention. In the reactor of complete mixing 12, the solution of collagen in acids 10 is mixed with the aqueous solution of calciumhydroxide 2 by the means of a stirrer 13.
Figure 5:
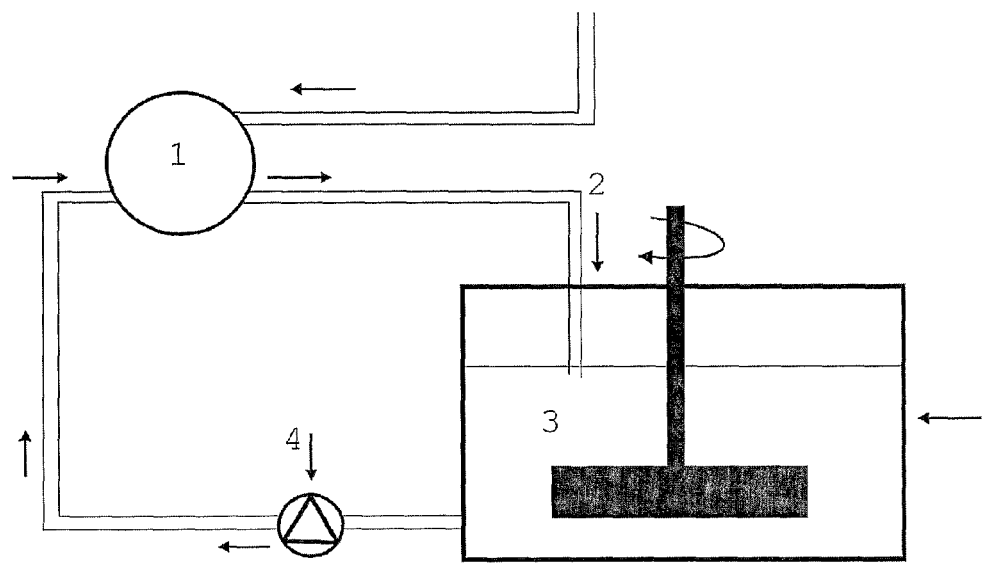
FIG. 5 shows a block-scheme of the second preferred embodiment of the method according to the invention. At the first stage of the first reactor of complete mixing 1, the solution of collagen in acids is mixed with circulating aqueous suspension of CaO (for example, due to tangential input of two flows of solutions). Then the mixture frontally moves in a pipe without compulsory agitation (a reactor for complete replacement 2) and enters the second reactor of complete mixing 3 with a stirrer and with a subsequent circulation of a flow and introduction of the mixture into reactor 1.
Figure 6:
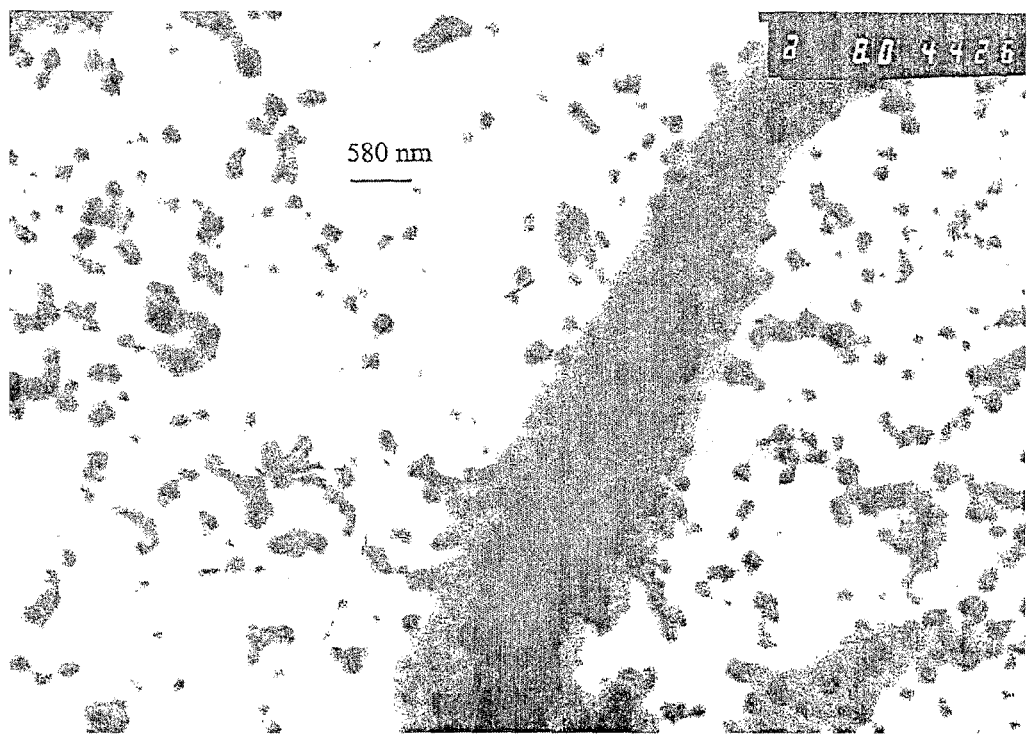
FIG. 6 shows an electron microscopic image of the hydroxyapatite particles prepared by mixing a two-component solution of collagen in $Na_3PO_4$ in water with a solution of $CaCl_2$. In the image small separate globules can be seen partially bound in small chain-like aggregates, or large "fibrils"-aggregates of fine globules and collagen.
Figure 7:
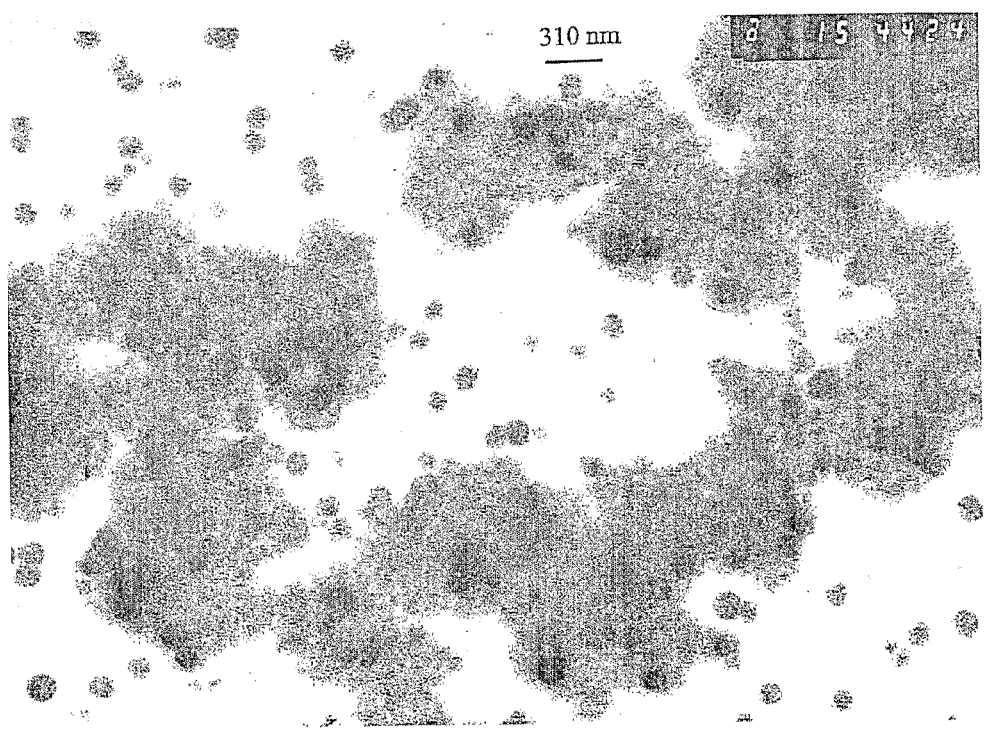
FIG. 7 shows the pattern of the hydroxyapatite particles prepared by mixing a solution of collagen in a mixture of $H_3PO_4$ and HCl with a solution of $Ca(OH)_2$ and NaOH. Fine separate globules of the biocomposite material and large collagen particles comprising small globules, forming long chain-like aggregates may be observed.
Figure 8:
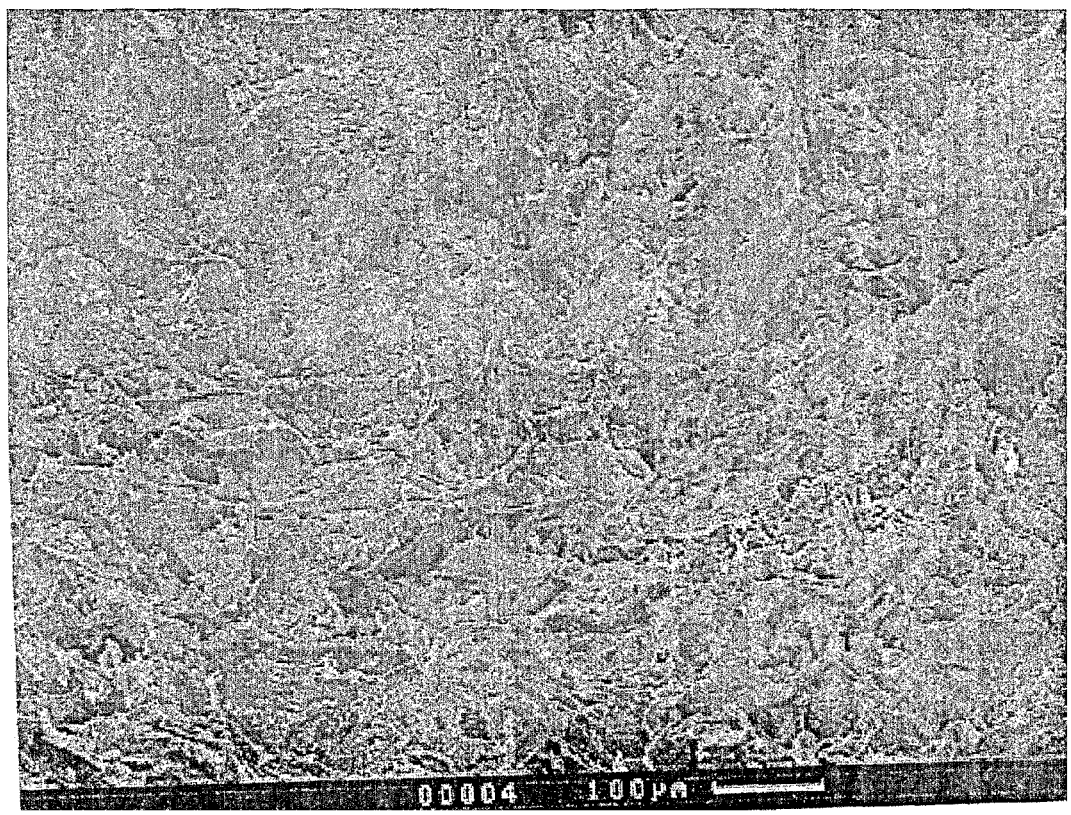
FIG. 8 shows the texture of the hydroxyapatite particles prepared by mixing a collagen solution in $H_3PO_4$ with $Ca(OH)_2$ and repeated mixing of the biocomposite material with an aqueous solution of collagen. The biocomposite material is produced as a fairly fragile sponge paste with a centrifuging time of 5 min.
Figure 9:
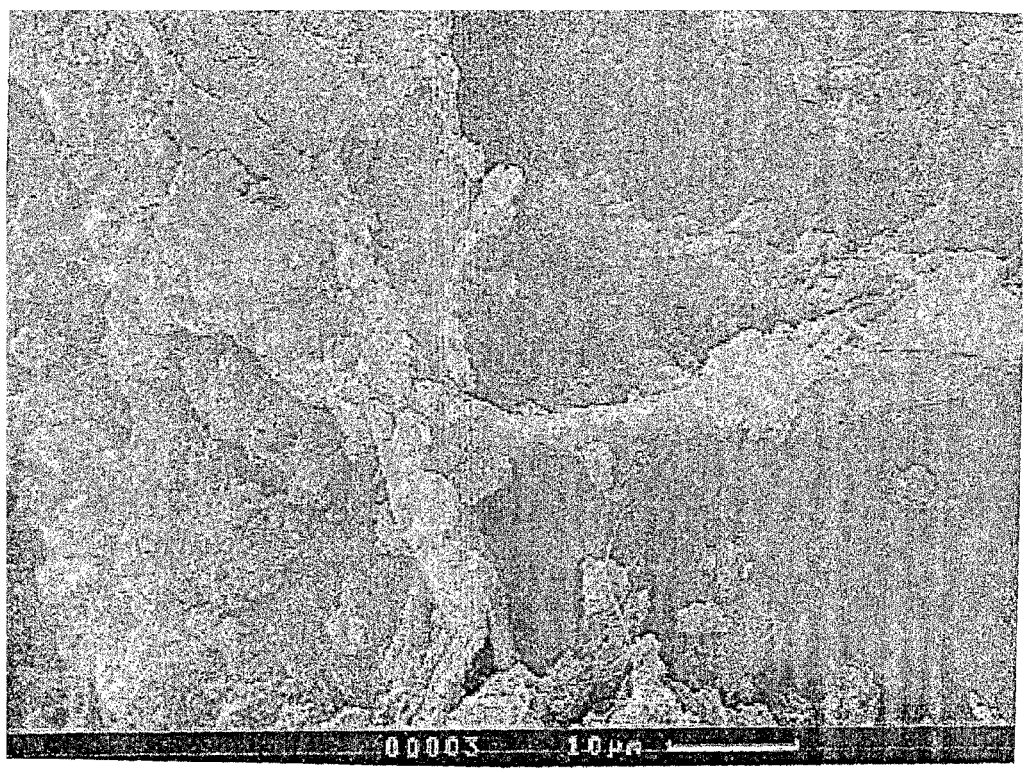
FIG. 9 shows the texture of the hydroxyapatite particles prepared by mixing a collagen solution in $H_3PO_4$ with $Ca(OH)_2$ and repeated mixing of the biocomposite material with an aqueous solution of collagen. The biocomposite material is produced as a fairly fragile sponge paste with a centrifuging time of 5 min. This picture is taken with a higher magnification than FIG. 8.
Figure 10:
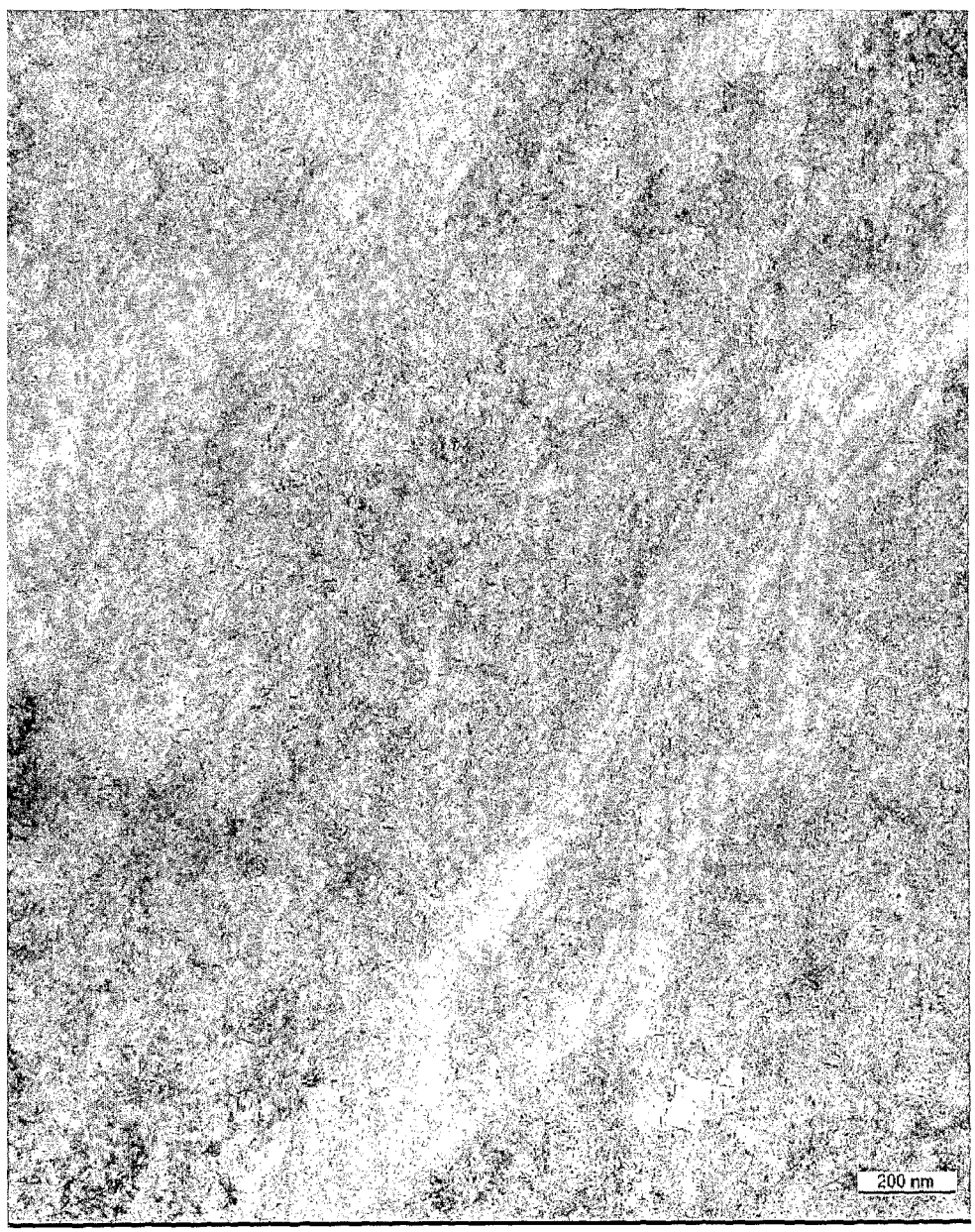
FIG. 10 shows the texture of the subnanosized hydroxyapatite particles in a freeze dryed mat. This picture is taken with a magnification that is so high, that the texture of the hydroxyapatite particles in the matrix is visible.

The following examples are given of the preferred embodiments of the methods according to the invention for producing subnanocrystalline hydroxyapatite in collagen matrix.

EXAMPLE 1

According to the First Preferred Embodiment of the Method of Synthesis

To produce the $Ca(OH)_2$ in aqueous solution, 1.12 g of CaO and 300 g of water are stirred for 15 min in a reactor by means of a blade mixer at a temperature of 22° C. The pH value of this solution comprising the calciumhydroxide is at 12.96. At the same time 100 ml water of analytical grade are added to 200 g of a 1% collagen solution. During 15 min the prepared collagen suspension is poured into the reactor by means of a pipette. The pH value of the resulting suspension attains at 12.86. After this during 15 min the phosphoric acid is added by the means of a hose pump until the pH value is 11.3. Now the solution is further stirred for 10 min and during 3 min phosphoric acid is added until the pH Value attains to 9.5. After further stirring for 12 minutes phosphoric acid is added during 5 min by the means of a hose pump until the pH value is 8.0 and after further stirring for 10 min phosphoric acid is added until the final pH value is 7.75. The amount of phosphoric acid necessary for the synthesis of the hydroxyapatite particles is 4.62 g.

EXAMPLE 2

According to the First Preferred Embodiment of the Method of Synthesis 10 l of solution $Ca(OH)_2$ with a concentration of 2.1-2 M/l is stirred in a reactor by means of a blade mixer at a Reynolds number $Re \approx 10^4$ and during 3-5 s a solution prepared from 1.0 g collagen in 12 ml of solution $H_3PO_4$ (10 m/l) is added. In 30 min a suspension of the biocomposite material or "HAP-collagen-product" with a concentration of 0.21% (S:L=1:500) is produced. Concentrating the suspension in a centrifuge at $G=8 \cdot 10^3$ during 10 min results in paste containing 10% of the "HAP-collagen-product" and 90% of water. Concentrating a suspension at $G=8 \cdot 10^3$ during 40 min results in paste containing about 28% of "HAP-collagen-product" and 72% of water. After sublimation drying of the first or the second paste, 21.1 g of dry "HAP-collagen-product" are produced that contains 4.7% of collagen and 95.3% of HAP subnanoparticles.

EXAMPLE 3

According to the First Preferred Embodiment of the Method of Synthesis 10 l of $Ca(OH)_2$ solution with a concentration of 2.1 to 2 M/l is stirred in a reactor by means of a blade mixer at a Reynolds number $Re \approx 10^4$ and during 3 to 5 s a solution prepared beforehand from 3.2 g of collagen in 12 ml of solution $H_3PO_4$ (10 M/l) (this corresponds approximately to solubility of collagen in chosen acid) is added. After 30 min a suspension of "HAP-collagen-product" with concentration of about 0.23% (S:L=1:400) is produced. After concentrating the suspension in a centrifuge with acceleration coefficient $G=8 \cdot 10^3$ during 10 min a paste containing 8% of "HAP-collagen-product" and 92% of mother liquor (water) is formed. After concentrating the suspension at $G=8 \cdot 10^3$ during 40 min a paste containing about 27% of "HAP-collagen-product" and 73% water is produced. In a result of sublimation drying of the first or the second paste, 23.3 g of dry powder of "HAP-collagen-product" containing 13.7% of collagen and 86.3% of HAP subnanoparticles are produced.

EXAMPLE 4

According to the First Preferred Embodiment of the Method of Synthesis

Into a 2 l reactor 700 ml of water, 100 ml of 2 M/l solution of $CaCl_2$ and 40 ml of 5 M/l solution of NaOH are poured. A solution is separately prepared from 9 g of collagen dissolved in 10 ml of 12 M/l solution of $H_3PO_4$ and 18 ml of 11.5 M/l solution of HCl. This solution is poured for 3 to 5 s into a reactor ($Re \approx 10^4$) with solution of $CaCl_2$ and NaOH accompanied with stirring by a blade mixer. In 30 min a suspension of the "HAP-collagen-product" with concentration of about 3.3% (S:L=1:300) is formed. After washing the product off the electrolyte NaCl and centrifuging at $G=8 \cdot 10^3$ during 45 min, a paste with a concentration of 28% of the "HAP-collagen-product" and 72% water is produced. After sublimation drying of the paste, 29 g of dry powder "HAP-collagen-product" containing 30% concentration of collagen and 70% of HAP subnanoparticles are produced.

EXAMPLE 5

According to the First Preferred Embodiment of the Method of Synthesis

Into a 3 l reactor 1 l water, 100 ml of 2 M/l solution of $CaCl_2$ and 140 ml of 5 M/l solution of NaOH are introduced. Separately a solution is prepared from 30 g collagen dissolved in 12 ml of 10 M/l solution of $H_3PO_4$ and 60 ml of 11.5 M/l solution of HCl that approximately corresponds to solubility (about 30%) of collagen in HCl. This solution is poured in 3 to 5 s into a reactor containing a solution of $CaCl_2$ and NaOH that is stirred with a blade stirrer at a Reynolds number $Re \approx 10^4$. Suspension of the "HAP-collagen-product" is produced with concentration of 3.7% (S:L=1:25.)

Further the suspension is washed off the electrolyte NaCl and concentrated by means of centrifuge at $G=8 \cdot 10^3$ during 10 min. In this process a paste with 7% concentration of the "HAP-collagen-product" and 93% water is produced. Centrifuging during 45 min results in formation of a paste with 25% concentration of the "HAP-collagen-product" and 75% of water. After sublimation drying of the pastes, 50 g of porous anhydrous mass are produced that contains 60% of collagen and 40% of HAP subnanoparticles.

EXAMPLE 6

According to the First Preferred Embodiment of the Method of Synthesis 2.5 l of water, 100 ml of 2 M/l solution of $CaCl_2$ and 370 ml of 5 M/l solution of NaOH are introduced into a reactor for 5 l. Separately 80 g of collagen are dissolved in 12 ml of 10 M/l solution of $H_3PO_4$ and 160 ml of 11.5 M/l solution of HCl. The prepared solution is poured into a reactor with a blade stirrer containing solution of $CaCl_2$ and NaOH. In 30 min a suspension of the "HAP-collagen-product" is produced with a 3.1% concentration (S:L=1:30). Afterwards the suspension is washed off the electrolyte NaCl and is concentrated by means of centrifuging at $G=8 \cdot 10^3$ during 45 min. In case a paste with 25% concentration of the "HAP-collagen-product" and 75% of water is obtained. After sublimation drying of the paste, 100 g porous anhydrous mass with 80% concentration of collagen and 20% of HAP subnanoparticles are produced.

EXAMPLE 7

According to the Second Preferred Embodiment of the Method of Synthesis

Water (10 l) is poured into a technological installation and while stirring 280 g CaO powder are fed. A solution is prepared separately of 20 g of collagen in 300 ml of 10 M/l $H_3PO_4$ is supplied into the first mixing reactor during 30 min. The holding time of the first reactor is 0.5 s with the flow rate of the mixture of 12 m/sec. Then the mixture is led into a second stage of the reactor of complete substitution with the holding time of 12 s and a pH=8.3. Further, the mixture is supplied into the third stage of the complete mixing with a pH value of 12.5. The outgoing produced mixture of HAP-collagen and calcium hydroxide is directed into the first stage to where phosphate solution of collagen is supplied until this solution is completely used. The recycling number is 12. The final pH value is 7.5 at this pH value the synthesis of hydroxyapatite particles is terminated.

In this case the suspension of the "HAP-collagen-product" with the concentration about 5.5% (C:L=1:17) is produced. After centrifuging at $G=8\cdot10^3$ during 45 min a paste is produced with 28% concentration of the "HAP-collagen-product" and 72% of water. After sublimation drying 580 g powder are produced with 13.7% concentration of collagen and 86.3% of HAP subnanoparticles.

EXAMPLE 8

According to the Second Preferred Embodiment of the Method of Synthesis

Into a technological installation one places 8 l of water and while stirring 56 g CaO and 18.4 l of 10 M/l solution of NaOH are produced. A solution separately prepared of 400 g of collagen in 60 ml of 10 M/l solution $H_3PO_4$ and 800 ml of 11.5 M/l solution of HCl is fed in 30 min into the first mixing reactor. The holding time in the first reactor is 0.3 s at a flow rate in the mixture of 15 m/sec. Further the mixture is fed into the reactor of the complete substitution of the second stage with the holding time of 12 s and pH=8.5. Then the mixture is supplied into the second reactor of the complete mixing with pH=12.2 of the third stage. The outgoing produced mixture of "HAP-collagen" and calciumhydroxide is directed into the first stage to where the phosphate solution of collagen is supplied until this solution is completely used. The recycling factor is 14. The final pH value of the solution is 7.8.

Thus the suspension of the "HAP-collagen-product" with a concentration of about 5.5% (S:L=1:17 is produced. After washing off the electrolyte NaCl and centrifuging at $G=8\cdot10^3$ during 40 min a paste with 25% concentration of the "HAP-collagen-product" and 75% of water is prepared. After sublimation and drying 500 g of anhydrous porous mass is produced with 80% concentration of collagen and 20% of HAP subnanoparticles.

The invention claimed is:

1. A method for producing hydroxyapatite (HAP) particles in a matrix, the method comprising:
    preparing an aqueous solution containing a matrix-building polymer and phosphoric acid,
    preparing an aqueous solution containing calcium hydroxide,
    feeding the polymer solution into the calcium hydroxide solution while subjecting the latter to mechanical action for synthesizing hydroxyapatite particles embedded in the matrix-building polymer,
    wherein the synthesis of the hydroxyapatite particles is started at a pH value of 8 to 9 and terminated at a pH value of 6 to 8, resulting in a suspension whose HAP particle length comes to mainly between 0.35 and 5 nm, mainly between 0.35 and 2.5 nm and/or mainly between 0.35 and 1.2 nm,
    wherein collagen and/or gelatine is used as the matrix building polymer, and
    wherein the aqueous solution of the matrix-building polymer contains HCl.

2. The method according to claim 1, wherein said suspension is held in a reactor for about 30 minutes before lowering the pH value.

3. The method according to claim 1, wherein the molar ratio of calcium to phosphorous is 1.67±0.3.

4. The method according to claim 1, wherein the hydroxyapatite particle synthesis is carried out at a temperature between 1° C. and 45° C.

5. The method according to claim 1, wherein the hydroxyapatite particle synthesis is carried out at a temperature between 20° C. and 25° C.

6. The method according to claim 1, wherein the final pH Value is adjusted by adding phosphoric acid.

7. The method according to claim 1, wherein the aqueous solution of calcium hydroxide exhibits a calcium hydroxide-to-water ratio of 1:10 to 1:1000.

8. The method according to claim 1, wherein for the synthesis of hydroxyapatite particles an aqueous solution of $CaCl_2$ and NaOH is used.

9. The method according to claim 1, wherein for the synthesis of HAP an aqueous solution of NaOH in an aqueous suspension of calcium hydroxide is used.

10. The method according to claim 1, wherein for the synthesis of the hydroxyapatite particles a polypeptide is used as the matrix building polymer.

11. The method according to claim 1, wherein the synthesis of the hydroxyapatite particles is carried out in a continuous periodical process.

12. The method according to claim 1 in which the synthesis of the hydroxyapatite particles is carried out comprising the steps of:
    mixing and holding the suspension comprising the calcium hydroxide, the matrix building polymer and the phosphoric acid in a first reactor thereby adjusting a defined alkaline first pH value,
    feeding the suspension into a second reactor for causing a phase transformation of the suspension, and
    feeding the suspension into a third reactor for mixing the suspension at a defined second pH value to then feed the mixture into a first reactor.

13. The method according to claim 12, wherein the holding time in the first reactor is 0.2 s to 0.8 s, the pH alkaline first pH value is adjusted to 8 to 9 the suspension is stirred with a rate of 10 m/s to 20 m/s.

14. The method according to claim 12, wherein the suspension is kept in the second stage during 10 s to 20 s at a pH value of 8 to 9 for producing the hydroxyapatite particles.

* * * * *

UNITED STATES PATENT AND TRADEMARK OFFICE
CERTIFICATE OF CORRECTION

PATENT NO.         : 8,691,273 B2                                                            Page 1 of 1
APPLICATION NO.    : 11/996254
DATED              : April 8, 2014
INVENTOR(S)        : Rudin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1692 days.

Signed and Sealed this

Twenty-ninth Day of September, 2015

Michelle K. Lee
*Director of the United States Patent and Trademark Office*